United States Patent [19]

Yale et al.

[11] 4,134,975
[45] Jan. 16, 1979

[54] STIMULATING THE CENTRAL NERVOUS SYSTEM

[75] Inventors: Harry L. Yale, New Brunswick, N.J.; Ramesh B. Petigara, Lansdale, Pa.

[73] Assignee: E. R. Squibb & Sons, Inc., Princeton, N.J.

[21] Appl. No.: 501,324

[22] Filed: Aug. 28, 1974

Related U.S. Application Data

[62] Division of Ser. No. 347,939, Apr. 4, 1973, Pat. No. 3,856,801.

[51] Int. Cl.$^2$ ............................................. A61K 31/44
[52] U.S. Cl. ................................................... 424/263
[58] Field of Search ........................................ 424/263

[56] References Cited

U.S. PATENT DOCUMENTS

| 3,123,614 | 3/1964 | Yale et al. | 260/296 H |
|---|---|---|---|
| 3,565,914 | 2/1971 | Yale et al. | 260/296 H |

*Primary Examiner*—Stanley J. Friedman
*Attorney, Agent, or Firm*—Lawrence S. Levinson; Merle J. Smith; Burton Rodney

[57] ABSTRACT

Compounds of the formula

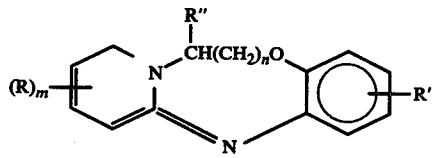

exhibit central nervous system stimulating properties and act as muscle relaxants.

1 Claim, No Drawings

STIMULATING THE CENTRAL NERVOUS SYSTEM

RELATED APPLICATION

This application is a divisional of application Ser. No. 347,939, filed Apr. 4, 1973, now U.S. Pat. No. 3,856,801.

OBJECTS OF THE INVENTION

It is an object of the present invention to provide new compounds having central nervous system (CNS) stimulating activity. Another object is to provide new compounds having muscle relaxant properties. A further object is to provide intermediates for the preparation of the final compounds of the invention. Yet another object is to provide a method for the preparation of both the intermediate and the final compounds of the present invention. Still another object is to provide a method for the administration of the final compounds of the invention. A still further object is to provide pharmaceutical compositions containing as active ingredients the final compounds of the present invention. These and other objects of the present invention will be apparent from the following description.

SUMMARY OF THE INVENTION

The compounds of the present invention have the following formula

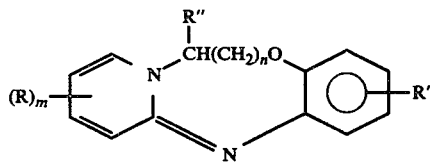

wherein m may be 1 or 2

R may be the same or different and may be hydrogen, halogen (F, Cl, or Br), alkyl of from 1 to 4 carbons, alkoxy of from 1 to 4 carbons, alkylthio of from 1 to 4 carbons, benzyl, phenethyl, phenyl, phenoxy, phenylmercapto or mono-substituted phenyl wherein the substituent may be halogen (F, Cl, Br or I), alkyl of from 1 to 4 carbons, alkoxy of from 1 to 4 carbons, or trifluoromethyl; provided that when R is halogen, R occupies only the 3- or 5- position in the original 2-aminopyridine;

R' may be hydrogen, halogen (F, Cl, Br or I), alkyl of from 1 to 4 carbons, alkoxy of from 1 to 4 carbons, alkylmercapto of from 1 to 4 carbons, alkylsulfonyl wherein the alkyl radical has from 1 to 4 carbons, phenyl, phenyloxy, sulfamoyl, dialkylamidosulfonyl wherein each alkyl radical may have from 1 to 4 carbons, trifluoromethyl, mono-substituted phenyl or mono-substituted phenyloxy wherein the substituent may be halogen (F, Cl, Br or I), alkyl of from 1 to 4 carbons, alkoxy of from 1 to 4 carbons or trifluoromethyl; provided that R' occupies the position para to the carbon atom joined to oxygen when R' is alkylsulfonyl, sulfamoyl, dialkylamidosulfonyl, phenyl, phenoxy, mono-substituted phenyl or mono-substituted phenoxy;

n may be 0 or 1;

and R'' may be alkyl of from 1 to 4 carbons, or hydrogen and pharmaceutically acceptable acid-addition salts thereof.

The foregoing compounds possess central nervous system stimulating properties and act as muscle relaxants.

DETAILED DESCRIPTION

The final compound I of the present invention may be prepared by reacting a 2-aminopyridine II wherein R is as previously defined with an o-bromophenoxyalkylene halide III wherein R'' is as previously defined and X is chlorine or bromine. This reaction takes place in any solvent or solvent mixture in which the reactants can be dissolved and which has a boiling point of at least about 100° C. Typical solvents are aromatic hydrocarbons, ethers, aliphatic alcohols or aryl-substituted aliphatic alcohols. Toluene and xylene are examples of suitable aromatic hydrocarbons. Monomethyl ether of diethylene glycol, dimethyl ether of diethylene glycol (diglyme), monomethyl ether of ethylene glycol or dimethyl ether of ethylene glycol (glyme) are examples of suitable ethers. n-Amyl alcohol is an example of a suitable aliphatic alcohol, while benzyl alcohol is an example of a suitable aryl-substituted aliphatic alcohol. Heating compounds II and III in a solvent as described above, or a mixture thereof, at temperatures from about 100° to about 140° C. for a period of several hours, typically from about 3 to about 24 hours produces a pyridinium compound IV. The latter is converted to an imino compound V by treating with a water miscible alcohol and an alkali metal alkoxide of up to 3 carbon atoms or an alkali metal carbonate. The reaction takes place at room temperature over a period of from about 1 to about 4 hours. Compound V may be converted to the final compound I by treating with a water miscible alcohol and an alkali metal alkoxide of up to 3 carbons in the presence of copper at a temperature of from about 60° to about 120° C. for several hours, typically from about 2 to about 4 hours. Alternatively, IV may be converted directly to I by heating at a temperature of from about 60° to about 120° C. for several hours, typically from about 1 to about 4 hours in the presence of potassium carbonate and copper in a solvent such as dimethylformamide, dimethylacetamide, dichlorobenzene, trichlorobenzene, or diethylbenzene. Alternatively, however, IV may be converted directly to I by heating at a temperature of from about 60° to about 120° C. for several hours, typically from about 1 to about 4 hours in the presence of an alkali metal hydroxide, alkali metal carbonate, tris-alkali metal phosphate, alkali metal metaborate or alkali metal tetraborate in a solvent comprising a mixture of water and a water miscible alcohol in the presence of copper. Specific examples of suitable compounds include LiOH, NaOH, KOH, RbOH, CsOH, $Na_2CO_3$, $K_2CO_3$, $Rb_2CO_3$, $Cs_2CO_3$, $Na_3PO_4$, $K_3PO_4$, $Rb_3PO_4$, $Cs_3PO_4$, $Na_2B_2O_4$, $Na_2B_4O_7$, $K_2B_2O_4$, and $K_2B_4O_7$. The ratios of water and alcohol in the mixture of water and a water miscible alcohol are such that a homogeneous single phase system results. The foregoing reaction sequence is illustrated by the following equations

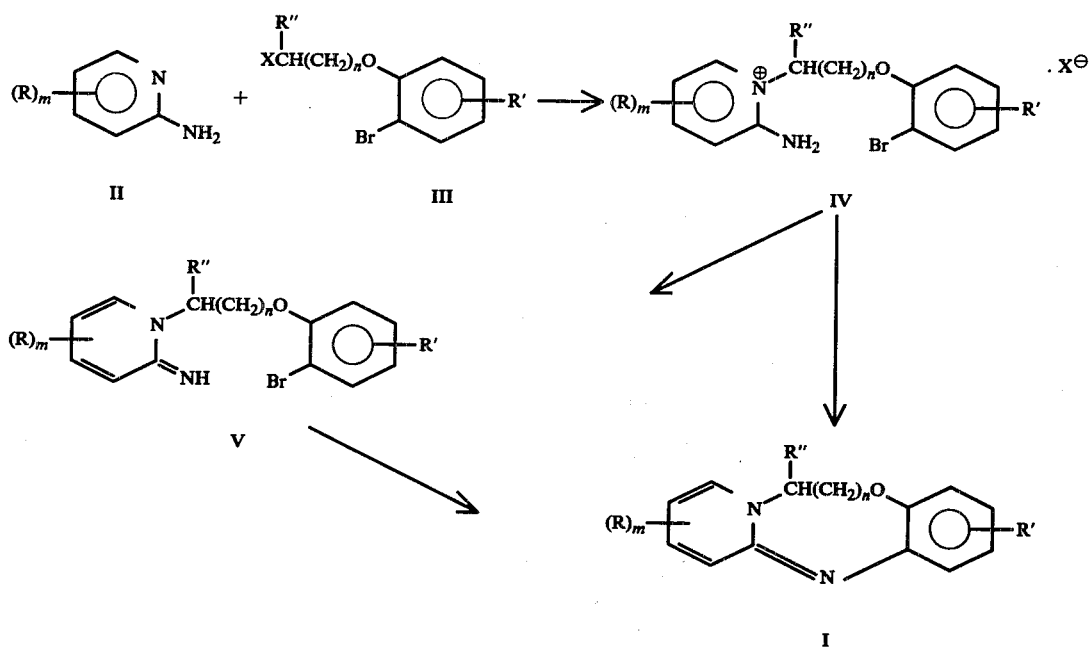

The intermediates of formula III wherein n is 0 may be prepared by refluxing about equimolar amounts of a 1,1-dibromoalkane or a 1-bromo-1-chloroalkane of 1 to 4 carbons VI with a saturated solution of $Na_2SO_3$ for a period of from about 40 to about 120 hours. The resulting 1-bromoalkane-1-sodium sulfonate VII is then reacted by heating with about equimolar amounts of an o-bromophenol VIII in the presence of aqueous alkali to yield a sodium o-bromophenoxyalkylene-sulfonate IX. Treatment of the latter with $PCl_5$ or $PBr_5$ at ambient temperature yields the corresponding o-bromophenoxyalkyl chloride or bromide X. The foregoing reaction sequence is illustrated by the following equations

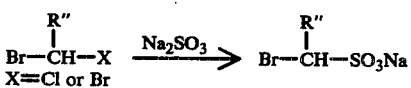

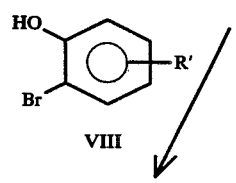

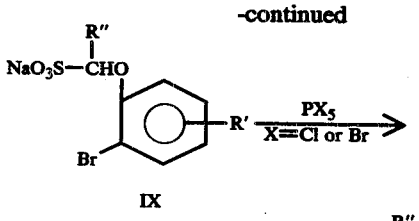

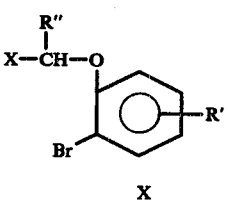

The intermediates of formula III wherein n is 1 may be prepared by reacting a 1-bromo-2-chloroalkane of formula XI with about equimolar amounts of a compound of formula VIII in the presence of aqueous alkali. Alternatively, a compound of formula XII may be prepared by reacting an o-bromophenoxyalkanol XIII with $PCl_5$ or $PBr_5$. The foregoing reaction sequence is illustrated by the following equations

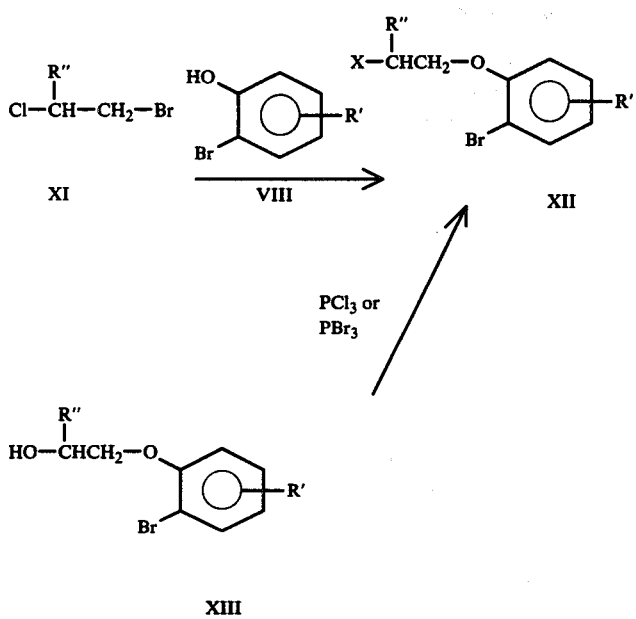

Compounds of formula VIII wherein R' is fluorine, CF$_3$ or alkylthio wherein the alkyl radical is from 1 to 4 carbons may be prepared by brominating a fluorophenol, a trifluoromethylphenol or an alkylthiophenol in the presence of Fe catalyst at from about 30° to about 40° C. From about 1 part by weight of iron to about 10 parts by weight of the substituted phenol are generally used. A halogenated solvent, e.g., chloroform or carbon tetrachloride, may be used in those cases where the substituted phenol is a solid at reaction temperatures. The foregoing reaction sequence is illustrated by the following equations

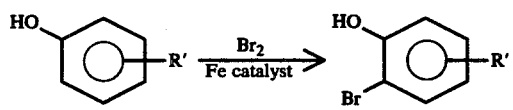

R' = —F, —CF$_3$ or —S—alkyl

Compounds of formula VIII wherein R' in the position para to the hydroxyl group is alkylsulfone, sulfamyl or dialkylsulfamyl may be prepared by the following sequence of reactions

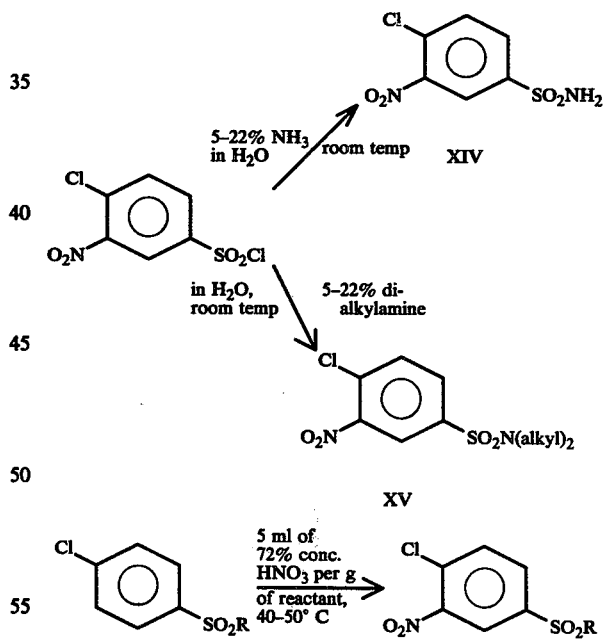

The chlorine atom in the compound of formula XIV, XV or XVI is replaced by a hydroxyl group by following the procedure of Pettit et al., J. Chem. Soc., 3852, 1954. Treatment of the resulting hydroxy derivative according to the procedure of Yale et al., J. Med. Chem., 13, 713, 1970, converts the nitro group to an amino group. Subjecting the resulting amino derivative to the Sandmeyer reaction serves to replace the amino group by a hydroxyl group to give the compound

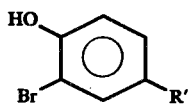

wherein R' is sulfamoyl, alkylsulfonyl or dialkylamidosulfonyl wherein the alkyl groups have from 1 to 4 carbon atoms.

Compounds of formula VIII wherein R' is phenyl or phenoxy are prepared by bromination of a hydroxybiphenyl or of a hydroxydiphenyl ether according to the procedure of Bradsher et al., J. Org. Chem., 22, 500 (1957) and Janssen et al., J. Org. Chem., 20, 1326-9 (1955). The foregoing reaction sequence is illustrated by the following equations

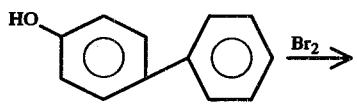

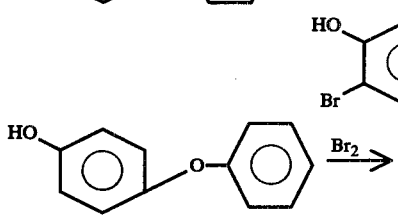

Compounds of formula VIII wherein R' is halophenyl, alkylphenyl, alkoxyphenyl, or trifluoromethylphenyl may be prepared by reacting an R'-substituted aniline with phenol according to the proceduce of Hirsch, Ber. 23, 3710 (1890). Bromination of the resulting p-(substituted phenyl)phenol by the procedure of Bradsher et al., supra. gives the o-bromo-p-(substituted phenyl)phenol. The foregoing reaction, sequence is illustrated by the following equations:

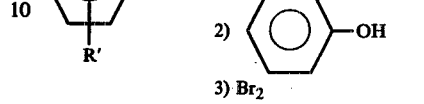

R' = halogen, alkyl, alkoxy or CF$_3$

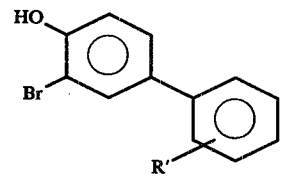

Compounds of formula VIII wherein R' is halophenoxy, alkylphenoxy, or trifluoromethylphenoxy may be prepared by the methods of Organic Syntheses Coll. Vol. III, p. 566 and Coll. Vol. II, p. 455, followed by the methods of Janssen et al. and Bradsher et al., supra. The reaction sequence is as follows:

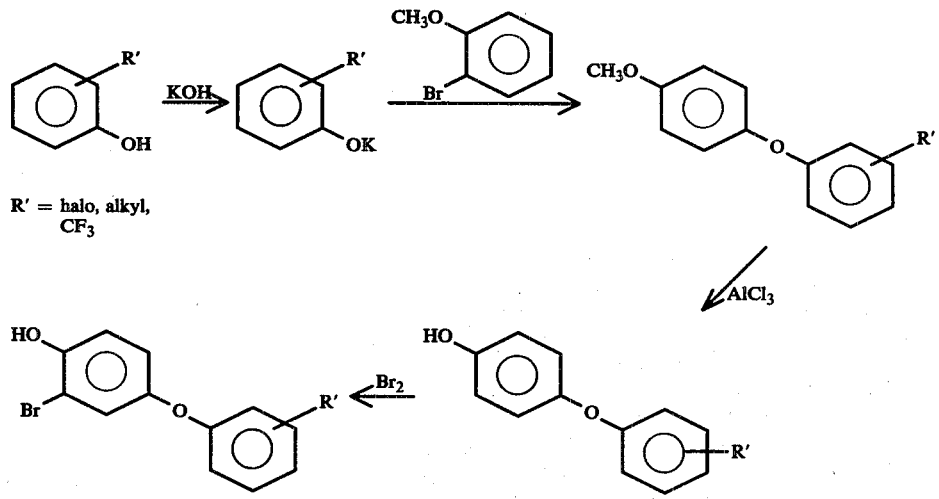

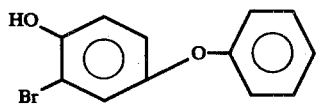

Compounds of formula VIII wherein R' is alkoxy-substituted phenyl may be prepared by reacting p-chloronitrobenzene with an alkoxy-substituted phenol in the presence of KOH, reducing the resulting p-(alkoxyphenoxy)-nitrobenzene to the corresponding amine and treating the latter with nitrous acid and water to convert the amino group to the hydroxyl group, and brominating the resulting p-(alkoxyphenoxy)phenol. The reaction sequence is as follows:

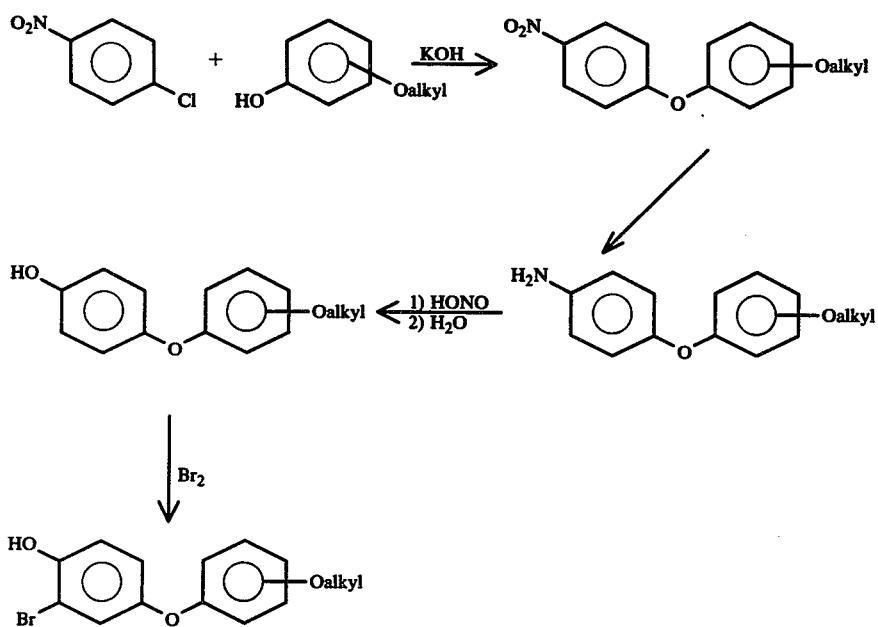

Starting materials of formula II wherein R is phenyl, halo-substituted phenyl, alkyl-substituted phenyl, alkoxy-substituted phenyl or trifluoromethyl-substituted phenyl may be prepared by heating 3-(N-acetamido-N-nitroso)pyridine XXIV with benzene, halo-substituted benzene, alkyl-substituted benzene, alkoxy-substituted benzene or trifluoromethyl-substituted benzene according to the procedure of Haworth et al., J. Chem. Soc., 1940, 372, and J. Chem. Soc., 1954, 4516. The product XXV is a 3-substituted pyridine wherein the N-acetamido-N-nitroso radical is replaced by a phenyl or substituted phenyl radical derived from the compound with which the 3-(N-acetamido-N-nitroso)pyridine is heated. The product of formula XXV is treated with sodamide according to the procedure of Chichibabin et al., J. Russ, Phys. Chem. Soc. 46, 1216 (1914), Chem. Zentr. II, 1064 (1915), to give the aminopyridines XXXII and XXXIII.

Compounds of formula II wherein R is F, or wherein one R is F and the other R is alkoxy, may be prepared by treating 3-aminopyridine XXVI, or 3-alkoxy-5-aminopyridine, with amyl nitrite and fluoroboric acid according to the procedure of Roe et al, JACS 69, 2443 (1947). The resulting 3-fluoropyridine XXVII is then treated with sodamide according to the procedure of Chichibabin et al, J. Russ, Phys. Chem. Soc. 46, 1216 (1914), Chem. Zentr. II, 1064 (1915) to yield a mixture of 2-amino-3-fluoropyridine and 2-amino-5-fluoropyridine which is separated by conventional procedures.

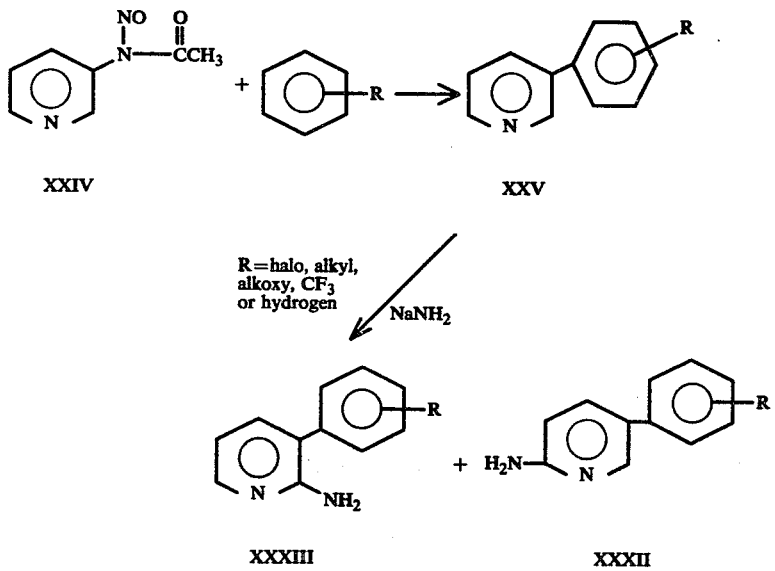

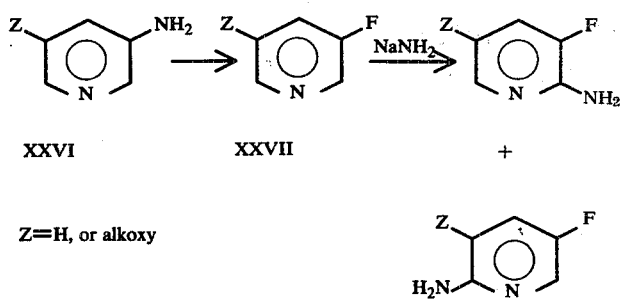

XXVI        XXVII        +

Z=H, or alkoxy

Compounds of formula II wherein R is halophenyl may be prepared by reacting a halo-substituted N-nitrosoacetanilide with pyridine according to the procedure of Bachmann et al., Organic Reactions, Vol. II, pp. 224-261. The resulting halo-substituted phenylpyridine is treated with sodamide according to the procedure of Chichibabin et al., supra. to give the desired halophenylsubstituted 2-aminopyridine. The reaction sequence is as follows:

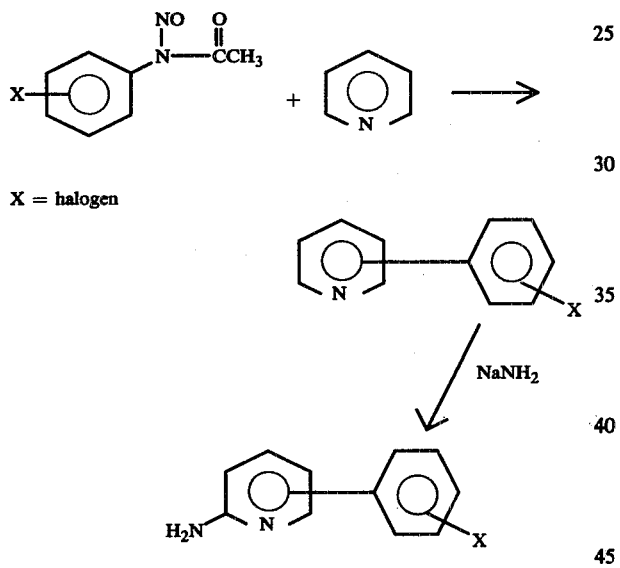

X = halogen

Compounds of formula II wherein R is phenylmercapto, alkylmercapto, benzyl, phenethyl or phenoxy may be prepared by treating a substituted pyridine of the formula

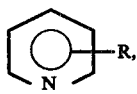

wherein R is a phenylmercapto, alkylmercapto, benzyl, phenethyl or phenoxy substituent occupying the 3-, 4-, 5-or 6-position, with sodamide according to the procedure of Chichibabin et al., supra.

The compounds of the present invention may be administered to mammalian species as central nervous system stimulants and as muscle relaxants. In the rat, responses to the stimulant activity of the compounds of the present invention include increased activity and body tremors. The muscle relaxant properties manifest themselves by responses that include decreased limb tone, decreased grip strength, and limb paralysis. In both the stimulant and muscle relaxant activities, the onset of activity is rapid, i.e., within about 15 minutes; the activity persists for about 2 hours or longer. In the rat the dosage range varies from about 6.25 to about 50 mg/kg for both activities, while in humans the dosage range varies from about 40 to about 2000 mg. daily in about four divided doses for both activities.

In addition to serving as intermediates for the preparation of compounds of formula I, the pyridinium compounds of formula IV are themselves effective bactericides.

Microbial bioassays, as described in "The Microbial World," by R. Y. Stanier, M. Doudoroff and E. A. Adelberg, Prentice-Hall, Inc., Englewood Cliffs, N.J., 3rd Ed., p. 858, are employed to determine the bactericidal properties of the pyridinium compounds IV of this invention. The bacteria employed include Staphylococcus aureus, 1, Streptococcus pyogenes, 2, Salmonella schottmuelleri, 3, Salmonella gallinarum, 4, Pseudomonas aeruginosa, 5, Proteus vulgaris, 6, Escherichia coli, 7, Pasturella multocida, 8, and Mycobacterium tuberculosis, 9.

In the procedure, a sterile agar plate is seeded with the test organism, and then a number of glass cylinders are placed on its surface, forming a series of little cups. A known dilution of the compounds of this invention is added to each cup and the entire plate is then incubated until significant bacterial growth has occured. The compounds of this invention diffuse out of the cup into the surrounding agar and produce a zone of inhibition. In this fashion it is possible to find the minimum inhibiting concentration (mic), of the compound that produces a recognizable zone of inhibition. The following summarizes the data.

| Micro-organism | mic of Pyridinium Compound Micrograms, (mcg)/ml | | | |
|---|---|---|---|---|
| | Compound of Ex. 1 | Compound of Ex. 4 | Compound of Ex. 22 | Compound of Ex. 98 |
| 1 | 3.13 | 12.5 | 6.25 | 6.25 |
| 2 | 12.5 | 50.0 | 50.0 | 25.0 |
| 3 | 12.5 | 50.0 | 12.5 | 12.5 |
| 4 | 6.25 | 25.0 | 12.5 | 12.5 |
| 5 | 12.5 | 25.0 | 25.0 | 25.0 |
| 6 | 12.5 | 25.0 | 25.0 | 25.0 |
| 7 | 3.13 | 25.0 | 12.5 | 6.25 |
| 8 | 6.25 | 12.5 | 25.0 | 12.5 |
| 9 | 0.39 | 6.25 | 1.57 | 0.78 |

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil or wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

As to the pharmaceutically acceptable salts, those coming within the purview of this invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicylic, succinic acid, theophylline, 8-chlorotheophylline, p-aminobenzoic, p-acetamidobenzoic, or methanesulfonic.

The following examples illustrate the present invention without, however, limiting the same thereto. All temperatures in the following examples as well as the preceding description are expressed in degrees Centigrade.

EXAMPLE 1

6H-Pyrido[1,2-c][1,3,5]benzoxadiazepine, hydrochloride

A. Sodium bromomethane sulfonate

A mixture of 372.0 g of dibromomethane and a saturated solution of 261.0 g of sodium sulfite in 750 ml of water is refluxed with stirring for about 80 hours. The reaction mixture is concentrated by distillation (600 ml of water is removed); the residue solidifies on standing. The solid, 608 g, is recrystallized from 200 ml of water to give about 380.0 g of the product, mp about 277°–281°.

B. (o-Bromophenoxy)methane sulfonic acid, sodium salt

To a solution of 61.3 g of o-bromophenol in aqueous NaOH solution [15.5 g of sodium hydroxide in 61 ml of water], is added 68.0 g of sodium bromomethanesulfonate. While stirring, the reaction mixture is slowly heated to 150°, in an oil bath, with simultaneous removal of water. In about 3 hours of heating, 61 ml of water is distilled, and the residue solidifies; this is further heated at 200° for about 2.5 hours. The solid is dissolved in 800 ml of warm water, the solution filtered and the filtrate adjusted to pH 5 and washed with 2 × 200 ml of ether. The aqueous phase is concentrated to 600 ml and cooled. The crystalline solid is filtered and dried in vacuo to give 63.3 g of the product, which is recrystallized from 600 ml of 90% aqueous ethanol to furnish about 57.5 g of the title product, mp about 282°–284°.

c. o-Bromo-α-chloroanisole

A mixture of 29.0 g of o-bromo-α-chloroanisole and 50.0 g of $PCl_5$ are thoroughly blended in a mortar. After about 10 minutes of continuous mixing, the mixture partly melts, a vigorous reaction occurs, and the whole turns to a liquid. The mixture is kept 15 minutes with occasional stirring, 700 ml of ether is added (a white solid separates) and the mixture is poured into 750 g of crushed ice. The ether solution is separated, washed, dried, and concentrated in vacuo to give about 21.0 g of a liquid residue. This is distilled under reduced pressure to give about 19.5 g of the colorless liquid product, $b_{2.0}$ 74°–75°, $n_D^{24.5}$ 1.5799.

D. 2-Amino-1-[(o-bromophenoxy)methyl]pyridinium chloride

To a solution of 7.1 g of 2-aminopyridine in 35 ml of xylene is added, dropwise, a solution of 11.1 g of o-bromo-α-chloroanisole in 45 ml of xylene. The mixture is warmed at 50° for 5 minutes and allowed to stir for 40 hours at room temperature. The solid is filtered and dried to give about 16.0 g of the product. This is recrystallized from 2-propanol to give about 14.0 g of the title product, mp 171°–173°.

E. 6H-Pyrido[1,2-c][1,3,5]benzoxadiazepine

A mixture of 9.5 g of 2-amino-1-[(o-bromophenoxy)methyl]pyridinium chloride, 8.3 g of potassium carbonate, 0.4 g of copper-bronze in 150 ml of n-propanol and 25 ml of water under $N_2$, is heated under reflux for 12 hours while stirring. The mixture is filtered hot and the deep yellow filtrate is concentrated to dryness. The residue is dissolved in 400 ml of ether, the ether solution is washed, dried and the solvent removed to give about 6.4 g of the crude yellow product. This is recrystallized from cyclohexane to give about 3.6 g of the title product, mp about 125°–127°.

F. 6H-Pyrido[1,2-c][1,3,5]-benzoxadiazepine, hydrochloride

To a solution of 1.0 g of 6H-pyrido[1,2-c][1,3,5]-benzoxadiazepine in 20 ml of 2-propanol is added 5.0 ml of 4.2N 2-propanolic hydrogen chloride. To the clear solution is added anhydrous ether until a turbidity forms. The pale yellow crystalline solid is filtered and recrystallized from acetonitrile to give about 1.0 g of the title compound, mp about 232°–234°.

EXAMPLE 2

6H-Pyrido[1,2-c][1,3,5]benzoxadiazepine

A. 1-(o-Bromophenoxymethyl)-1,2-dihydro-2-iminopyridine

A suspension of 7.0 g of the product from Example 1D, 5.6 g of micronized, anhydrous potassium carbonate, and 175 ml of anhydrous n-propanol is stirred and heated under reflux for about eight hours, filtered hot, and the filtrate concentrated to dryness in vacuo. The residue, about 6.3 g, is dissolved in 150 ml of ether, the ether solution is washed with water, saturated aqueous sodium chloride, dried and concentrated to give 1-(o-bromophenoxymethyl)-1,2-dihydro-2-iminopyridine, m.p. about 62°–64°. Recrystallization from pentane gives about 5.8 g of the pure product, m.p. about 63°–64°.

B. 6H-Pyrido[1,2-c][1,3,5]benzoxadiazepine

To a solution of 4.65 g of the product from A in 150 ml of n-propanol is added 0.20 g of copper bronze and 5.6 g of micronized, anhydrous, potassium carbonate, and the stirred suspension is heated under reflux for about ten hours. Workup as in Example 1E gives about 2.78 g of the title compound, m.p. about 125°–127°.

EXAMPLES 3–13

Following the procedure of example 1 but substituting for 2-aminopyridine in part D the substituted pyridine listed below, there is obtained the correspondingly substituted compound of formula IV wherein R' and R" are hydrogen and n=0 which compound is then converted to the correspondingly substituted compound of formula I:

3. 4-chloro-pyridin-2-amine (Cl on pyridine ring, NH2)

4. 4-bromo-pyridin-2-amine (Br on pyridine ring, NH2)

5. CH3CH2O-substituted pyridine with NH2

6. CH3CH2-substituted pyridine with NH2

7. (CH2)3CH3-substituted pyridine with NH2

8. CH3(CH2)2-substituted pyridine with NH2

9. C(CH3)3-substituted pyridine with NH2

10. (CH3)3C-substituted pyridine with NH2

11. phenyl-substituted pyridine with NH2

12. (CH2)3CH3-substituted pyridine with NH2

13. (CH2)2CH3-substituted pyridine with NH2

EXAMPLES 14–23

Following the procedure of example 1A through 1D but substituting for 2-aminopyridine the substituted pyridine listed below, there is obtained the correspondingly substituted compound of formula IV, which following the procedure of example 2, part A, is converted to the correspondingly substituted compound of formula V which is then converted to the correspondingly substituted compound of formula I by following the procedure of example 2, part B.

14. Br-substituted pyridine with NH2

15. OCH2CH3-substituted pyridine with NH2

16. CH3CH2O-substituted pyridine with NH2

17. CH2CH3-substituted pyridine with NH2

18. CH3(CH2)2-substituted pyridine with NH2

19. CH3(CH2)3-substituted pyridine with NH2

20. OCH3-substituted pyridine with NH2

21. 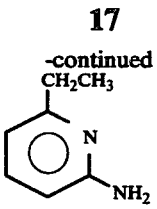

22. 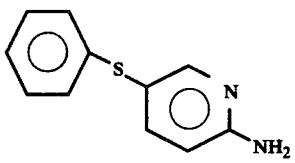

23. 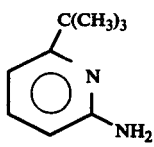

EXAMPLE 24

2-Chloro-6H-pyrido[1,2-c][1,3,5]benzoxadiazepine hydrochloride

A. 2-Bromo-4-chlorophenoxymethanesulfonic acid, sodium salt

To a solution of 75.0 g of 2-bromo-4-chlorophenol in 65 ml of water is added 16.0 g of sodium hydroxide and 100 g of bromomethanesulfonic acid, sodium salt. The procedure of Example 1, part B, is followed to give about 74.5 g of 2-bromo-4-chlorophenoxymethanesulfonic acid, sodium salt, m.p. above 315°.

B. 2-Bromo-4-chlorophenyl chloromethyl ether

A mixture of 71.0 g of the product from A and 110.0 g of phosphorus pentachloride is reacted as in Example 1, part C, to give about 55.7 g of 2-bromo-4-chlorophenyl chloromethyl ether, m.p. about 56.0°–57.5°.

C. 2-Amino-1-[(2-bromo-4-chlorophenoxy)methyl]-pyridinium choride

To a solution of 14.1 g of 2-aminopyridine in 180 ml of warm, anhydrous xylene is added 25.6 g of the product from B in 70 ml of anhydrous xylene and the mixture is stirred for about four hours at room temperature and then at 100° for about two hours to give about 33.0 g of 2-amino-1-[(2-bromo-4-chlorophenoxy)methyl]-pyridinium chloride, m.p. about 237°–239°.

D. 2-Chloro-6H-pyrido[1,2-c][1,3,5]benzoxadiazepine hydrochloride

A mixture of 14.0 g of 2-amino-1-[(2-bromo-4-chlorophenoxy)methyl]pyridinium chloride, 11.1 g of micronized, anhydrous potassium carbonate, 0.4 g of copper bronze, and 350 ml of anhydrous n-propanol is stirred and heated under reflux for about eight hours, filtered hot, and the deep yellow filtrate is concentrated to dryness in vacuo. Workup gives about 6.8 g of 2-chloro-6H-pyrido[1,2-c][1,3,5]benzoxadiazepine, m.p. about 175–177°.

To the above base, 2.0 g in 50 ml of warm 2-propanol, is added about 5.0 ml of 4.8N 2-propanolic hydrogen chloride. The solid that separates is filtered to give about 2.2 g of product. This is recrystallized from a mixture of acetonitrile and absolute ethanol to give about 1.9 g of the title compound, m.p. about 303–305° (dec.).

EXAMPLES 25–64

Following the procedure of example 24 but substituting for 2-bromo-4-chlorophenol the substituted 2-bromophenol listed in column I, there is obtained the correspondingly substituted compound from parts B and C, and finally the compound of the following formula wherein R' and the position it occupies are indicated in column II.

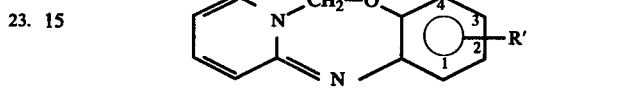

| Ex. | I | II |
| --- | --- | --- |
| 25. | 2,4-dibromophenol | 2-bromo |
| 26. | 2,6-dibromophenol | 4-bromo |
| 27. | 2-bromo-4-iodophenol | 2-iodo |
| 28. | 2-bromo-4-methylphenol | 2-methyl |
| 29. | 2-bromo-6-methylphenol | 4-methyl |
| 30. | 2-bromo-3-chlorophenol | 1-chloro |
| 31. | 2-bromo-5-chlorophenol | 3-chloro |
| 32. | 2-bromo-4-n-butylphenol | 2-n-butyl |
| 33. | 2-bromo-4-i-butylphenol | 2-i-butyl |
| 34. | 2-bromo-4-n-butoxyphenol | 2-n-butoxy |
| 35. | 2-bromo-6-fluorophenol | 4-fluoro |
| 36. | 2-bromo-5-fluorophenol | 3-fluoro |
| 37. | 2-bromo-4-fluorophenol | 2-fluoro |
| 38. | 2-bromo-4-(methylmercapto)phenol | 2-(methylmercapto) |
| 39. | 6-bromo-α,α,α-trifluoro-m-cresol | 3-trifluoromethyl |
| 40. | 6-bromo-α,α,α-trifluoro-o-cresol | 4-trifluoromethyl |
| 41. | 6-bromo-α,α,α-trifluoro-p-cresol | 2-trifluoromethyl |
| 42. | 2-bromo-3-(ethylmercapto)phenol | 1-(ethylmercapto) |
| 43. | 2-bromo-4-phenylphenol | 2-phenyl |
| 44. | 2-bromo-3-trifluoromethylphenol | 1-trifluoromethyl |
| 45. | 2-bromo-4-(p-fluorophenyl)phenol | 2-(p-fluorophenyl) |
| 46. | 2-bromo-4-phenoxyphenol | 2-phenoxy |
| 47. | 2-bromo-4-(o-fluorophenyl)phenol | 2-(o-fluorophenyl) |
| 48. | 2-bromo-4-(o-chlorophenyl)phenol | 2-(o-chlorophenyl) |
| 49. | 2-bromo-4-(m-bromophenyl)phenol | 2-(m-bromophenyl) |
| 50. | 2-bromo-4-(p-iodophenyl)phenol | 2-(p-iodophenyl) |
| 51. | 2-bromo-4-(m-fluorophenyloxy)phenol | 2-(m-fluorophenyloxy) |
| 52. | 2-bromo-4-(p-chlorophenyloxy)phenol | 2-(p-chlorophenyloxy) |
| 53. | 2-bromo-4-(m-iodophenyloxy)phenol | 2-(m-iodophenyloxy) |
| 54. | 2-bromo-4-(o-bromophenyloxy)phenol | 2-(o-bromophenyloxy) |
| 55. | 2-bromo-4-(o-methylphenyl)phenol | 2-(o-methylphenyl) |
| 56. | 2-bromo-4-(m-ethylphenyl)phenol | 2-(m-ethylphenyl) |
| 57. | 2-bromo-4-(p-methoxyphenyl)phenol | 2-(p-methoxyphenyl) |
| 58. | 2-bromo-4-(o-propoxyphenyl)phenol | 2-(o-propoxyphenyl) |
| 59. | 2-bromo-4-(p-trifluoromethylphenyl)phenol | 2-(p-trifluoromethylphenyl) |
| 60. | 2-bromo-4-sulfamoylphenol | 2-sulfamoyl |
| 61. | 2-bromo-4-dimethylamidosulfonylphenol | 2-dimethylamidosulfonyl |
| 62. | 2-bromo-4-dibutylamidosulfonylphenol | 2-dibutylamidosulfonyl |
| 63. | 2-bromo-4-ethylsulfonylphenol | 2-ethylsulfonyl |
| 64. | 2-bromo-4-propylsulfonylphenol | 2-propylsulfonyl |

EXAMPLES 65–68

Following the procedure of example 1 but substituting for dibromomethane the compound listed in column I, there is obtained the compound of the following formula

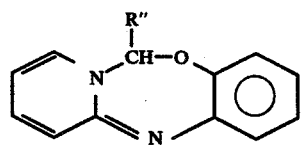

wherein R" is as indicated in column II.

| Example | I | II (R") |
|---|---|---|
| 65. | 1,1-dibromoethane | —CH₃ |
| 66. | 1,1-dibromoisobutane | —CH(CH₃)CH₃ |
| 67. | 1,1-dibromopropane | —CH₂CH₃ |
| 68. | 1,1-dibromopentane | —(CH₂)₃CH₃ |
| 69. | 1,1-dibromobutane | —CH₂CH₂CH₃ |
| 70. | 1,1-dibromoisopentane | —CH₂CH(CH₃)CH₃ |

EXAMPLES 71–97

Following the procedure of example 1 but substituting for 2-aminopyridine in part D an equivalent amount of the substituted pyridine listed in column I, there is obtained the correspondingly substituted pyridinium chloride (from part D), the correspondingly substituted base (from part E), and the correspondingly substituted hydrochloride salt (from part F). The substituent and the position it occupies in the final porudct of the formula

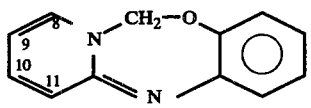

are indicated in column II.

| Example | I | II |
|---|---|---|
| 71. | 2-amino-3-phenylpyridine | 11-phenyl |
| 72. | 2-amino-3-(o-chlorophenyl)pyridine | 11-(o-chlorophenyl) |
| 73. | 2-amino-4-(m-bromophenyl)pyridine | 10-(m-bromophenyl) |
| 74. | 2-amino-5-(p-fluorophenyl)pyridine | 9-(p-fluorophenyl) |
| 75. | 2-amino-6-(m-iodophenyl)pyridine | 8-(m-iodophenyl) |
| 76. | 2-amino-3-(o-tolyl)pyridine | 11-(o-tolyl) |
| 77. | 2-amino-5-(p-ethylphenyl)pyridine | 9-(p-ethylphenyl) |
| 78. | 2-amino-3-(m-propoxyphenyl)pyridine | 11-(m-propoxyphenyl) |
| 79. | 2-amino-5-(p-butoxyphenyl)pyridine | 9-(p-butoxyphenyl) |
| 80. | 2-amino-3-(p-trifluoromethylphenyl)pyridine | 11-(p-trifluoromethylphenyl) |
| 81. | 2-amino-3-(methylmercapto)pyridine | 11-(methylmercapto) |
| 82. | 2-amino-6-(phenylmercapto)pyridine | 8-(phenylmercapto) |
| 83. | 2-amino-5-(phenylmercapto)pyridine | 9-(phenylmercapto) |
| 84. | 2-amino-4-(phenylmercapto)pyridine | 10-(phenylmercapto) |
| 85. | 2-amino-3-(phenylmercapto)pyridine | 11-(phenylmercapto) |
| 86. | 2-amino-6-(methylmercapto)pyridine | 8-(methylmercapto) |
| 87. | 2-amino-5-(butylmercapto)pyridine | 9-(butylmercapto) |
| 88. | 2-amino-5-(propylmercapto)pyridine | 9-(propylmercapto) |
| 89. | 2-amino-4-(methylmercapto)pyridine | 10-(methylmercapto) |
| 90. | 2-amino-4-(ethylmercapto)pyridine | 10-(ethylmercapto) |
| 91. | 2-amino-4-(ethylmercapto)-6-methylpyridine | 10-(ethylmercapto)-8-methyl |
| 92. | 2-amino-3-(phenethyl)pyridine | 11-)phenethyl) |
| 93. | 2-amino-4-benzylpyridine | 10-benzyl |
| 94. | 2-amino-5-(phenethyl)pyridine | 9-(phenethyl) |
| 95. | 2-amino-6-benzylpyridine | 8-benzyl |
| 96. | 2-amino-6-phenoxypyridine | 8-phenoxy |
| 97. | 2-amino-4-phenoxypyridine | 10-phenoxy |

EXAMPLE 98

6,7-Dihydro-7-methyl-10-phenethylpyrido[1,2-d][1,4,6]benzoxadiazocine

A. o-Bromophenyl 2-chloropropyl ether

To a solution of 23.0 g of sodium metal in 500 ml of absolute ethanol is added in about 0.5 hour a solution of 173.0 g of o-bromophenol in 250 ml of absolute ethanol. The mixture is stirred and heated under reflux for about 0.5 hour, cooled to 0°, and treated, dropwise, with 157.5 g of 1-bromo-2-chloropropane. The last addition requires about 1 hour. The mixture is stirred at 0° for about 2 hours and slowly warmed to reflux during about 2 hours, heated under reflux for about 2 hours, filtered from the precipitated sodium bromide, and the filtrate is concentrated in vacuo at 40° to give about 240.2 g of o-bromophenyl 2-chloropropyl ether as a mobile, colorless liquid.

B.

2-Amino-1-[2'-(o-bromophenoxy-1'-methylethyl)]-5-phenethylpyridinium chloride

A solution of 40.1 g of 2-amino-5-phenethylpyridine and 50.0 g of o-bromophenyl 2-chloropropyl ether and 200 ml of anhydrous toluene is heated under reflux for about 6 hours, cooled, and the crystalline product filtered to give about 73.2 g of 2-amino-1-[2'-(o-bromophenoxy-1'-methylethyl)]-5-phenethylpyridinium chloride as a colorless, crystalline solid.

C.

1-[2'-(o-Bromophenoxy-1'-methylethyl)]-1,2-dihydro-2-imino-5-phenethylpyridine

To a solution of 9.0 g of the product from B in 100 ml of anhydrous n-propanol is added 2.8 g of anhydrous, micronized potassium carbonate and the mixture stirred and heated under reflux for about 1 hour. The hot suspension is filtered and the filtrate concentrated to give a pale yellow solid. This is recrystallized from cyclohexane to give about 6.3 g of 1-[2'-(o-bromophenoxy-1'-methylethyl)]-1,2-dihydro-2-imino-5-phenethylpyridine as a pale yellow crystalline solid.

D.

6,7-Dihydro-7-methyl-10-phenethylpyrido[1,2-d][1,4,6]benzoxadiazocine

The product from C, 3.69 g, 50 ml of anhydrous n-propanol, 2.8 g of anhydrous, micronized potassium carbonate, and 0.25 g of copper bronze are stirred and heated under reflux for about 6 hours, filtered hot, and the deep, yellow colored filtrate is concentrated to dryness in vacuo at 40°. The deep yellow-colored solid is recrystallized from ligroin to give about 2.42 g of 6,7-dihydro-7-methyl-10-phenethylpyrido[1,2-d][1,4,6]-benzoxadiazocine.

Preparation of capsule formulation

| Ingredient | Milligrams per Capsule |
|---|---|
| 6H-Pyrido[1,2-c][1,3,5]benzoxadiazepine, hydrochloride | 400 |
| Starch | 80 |

The active ingredient, starch and magnesium stearate are blended together. The mixture is used to fill hard shell capsules of a suitable size at a fill weight of 485 milligrams per capsule.

Preparation of tablet formulation

| Ingredient | Milligrams per Tablet |
|---|---|
| 2-Chloro-6H-pyrido[1,2-c][1,3,5] benzoxadiazepine hydrochloride | 300 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 300 milligrams of active ingredient.

Preparation of oral syrup formulation

| Ingredient | Amount |
| --- | --- |
| 6,7-Dihydro-7-methyl-10-phenethylpyrido-[1,2-d][1,4,6]benzodiazocine | 500 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.D. & Co. No. 2) | 10 mg. |
| Cherry flavor | 50 mg. |
| Distilled water | 100 ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:

1. A method of stimulating the central nervous system in a mammalian species comprising administering systemically to a mammalian host an effective amount of a compound of the formula

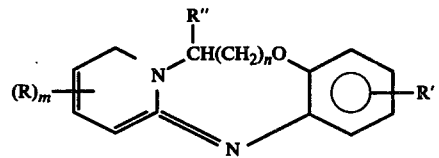

wherein m is 1 or 2

R is the same or different and is hydrogen, halogen (F, Cl, or Br), alkyl of from 1 to 4 carbons, alkoxy of from 1 to 4 carbons, alkylthio of from 1 to 4 carbons, benzyl, phenethyl, phenyl, phenoxy, phenylmercapto or mono-substituted phenyl wherein the substituent may be halogen (F, Cl, Br or I), alkyl of from 1 to 4 carbons, alkoxy of from 1 to 4 carbons, or trifluoromethyl; provided that when R is halogen, R occupies only the 3- or 5-position in the original 2-aminopyridine;

R' is hydrogen, halogen (F, Cl, Br or I), alkyl of from 1 to 4 carbons, alkoxy of from 1 to 4 carbons, alkylmercapto of from 1 to 4 carbons, alkylsulfonyl wherein the alkyl radical has from 1 to 4 carbons, phenyl, phenyloxy, sulfamoyl, dialkylamidosulfonyl wherein each alkyl radical may have from 1 to 4 carbons, trifluoromethyl, mono-substituted phenyl or mono-substituted phenyloxy wherein the substituent may be halogen (F, Cl, Br or I), alkyl of from 1 to 4 carbons, alkoxy of from 1 to 4 carbons or trifluoromethyl; provided that R' occupies the position para to the carbon atom joined to oxygen when R' is alkylsulfonyl, sulfamoyl, dialkylamidosulfonyl, phenyl, phenoxy, mono-substituted phenyl or mono-substituted phenoxy;

n is 0 or 1;

and R" is hydrogen or alkyl of from 1 to 4 carbons, or a pharmaceutically acceptable acid-addition salt thereof.

* * * * *

UNITED STATES PATENT AND TRADEMARK OFFICE
CERTIFICATE OF CORRECTION

PATENT NO. : 4,134,975

DATED : January 16, 1979

INVENTOR(S) : Harry L. Yale et al.

It is certified that error appears in the above—identified patent and that said Letters Patent are hereby corrected as shown below:

In the Abstract, the structure should read

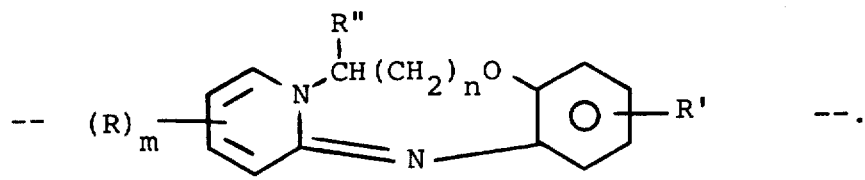

Column 8, line 4, after "reaction" delete the comma.

Column 19, Ex. 92, Column II should read --11-(phenethyl)--.

Column 20, in the table entitled "Preparation of capsule formulation", insert the following

| Ingredient | Milligrams per Capsule |
|---|---|
| -- Magnesium stearate | 5                    --. |

Column 21, in the table entitled "Preparation of oral syrup formulation, after "Distilled water" insert --qs to--.

UNITED STATES PATENT AND TRADEMARK OFFICE
CERTIFICATE OF CORRECTION

PATENT NO. : 4,134,975
DATED : January 16, 1979
INVENTOR(S) : Harry L. Yale et al.

It is certified that error appears in the above-identified patent and that said Letters Patent are hereby corrected as shown below:

Column 22, the structure in Claim 1 should read

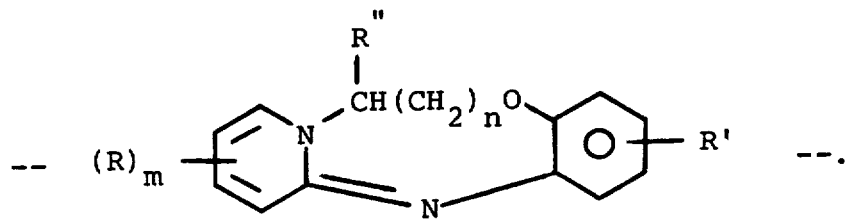

Signed and Sealed this

Third Day of July 1979

[SEAL]

Attest:

LUTRELLE F. PARKER

Attesting Officer        Acting Commissioner of Patents and Trademarks